United States Patent [19]

Freed et al.

[11] 4,320,057

[45] Mar. 16, 1982

[54] ARYL—PYRROLO—THIAZEPIN—DIONES AND ARYL—PIPERIDINO—THIAZEPIN—DIONES

[75] Inventors: Meier E. Freed, Paoli; James L. Diebold, Norristown, both of Pa.

[73] Assignee: American Home Products Corporation, New York, N.Y.

[21] Appl. No.: 247,462

[22] Filed: Mar. 25, 1981

Related U.S. Application Data

[62] Division of Ser. No. 161,967, Jun. 23, 1980.

[51] Int. Cl.³ ............................................ C07D 513/14

[52] U.S. Cl. ...................... 260/239.3 B; 260/326.47; 544/47; 546/226; 424/274; 424/256; 424/246; 424/267

[58] Field of Search .................... 260/239.3 B; 544/47

[56] References Cited

U.S. PATENT DOCUMENTS 4,192,945  3/1980  Ondetti ........................ 260/239.3 B Primary Examiner—Robert T. Bond
Attorney, Agent, or Firm—Richard K. Jackson

[57] ABSTRACT

Aryl-1-mercaptoalkanoylproline and homoproline derivatives and their cyclized thiazadione heterocyclic analogues reduce blood pressure in animals by ACE inhibition.

4 Claims, No Drawings

ARYL—PYRROLO—THIAZEPIN—DIONES AND ARYL—PIPERIDINO—THIAZEPIN—DIONES

This is a division of application Ser. No. 161,967 filed June 23, 1980.

BRIEF DESCRIPTION OF THE INVENTION

The compounds of this invention, certain aryl-1-mercaptoalkanoyl-homoproline and aryl-1-mercaptoalkanoyl-proline derivatives and their cyclized thiazadione heterocyclic analogues, reduce blood pressure in animals. They function as inhibitors of angiotensin converting enzyme in that they block C-terminal cleavage of the histidyl[9]-leucine[10] dipeptide from angiotensin I, thereby decreasing conversion to the strong pressor octapeptide antiotensin II.

DETAILED DESCRIPTION OF THE INVENTION

In accordance with this invention there is provided a group of hypotensive agents of the formula:

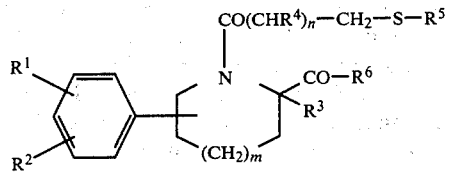

wherein
  $R^1$ and $R^2$ are, independently, hydrogen, alkyl of one to six carbon atoms, alkoxy of one to six carbon atoms, or halo;
  $R^3$ is hydrogen or alkyl of one to six carbon atoms;
  $R^4$ is hydrogen or alkyl of one to six carbon atoms;
  $R^5$ is hydrogen, alkanoyl of two to six carbon atoms or aroyl of six to ten carbon atoms;
  $R^6$ is —OH or —OM where M is a pharmaceutically acceptable cation;
  m is one of the integers 0 or 1;
  n is one of the integers 0, 1 or 2;
and the correspondingly substituted thiazadione derivatives of the formula

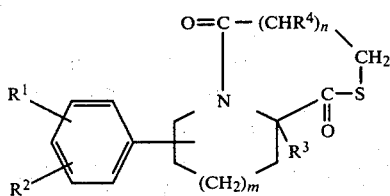

The preferred compounds of the invention are those of the preceding formulae in which $R^1$ and $R^2$ are, independently, hydrogen or alkoxy of one to three carbon atoms (the most preferred alkoxy substituent is methoxy); $R^5$ is hydrogen or methyl; $R^4$ is hydrogen or alkyl of one to three carbon atoms; $R^5$ is hydrogen, acetyl or benzoyl; $R^6$ is —OH or —OM where M is sodium, potassium or NH$_4$; m is zero; n is one; and the substituted phenyl moiety is ortho to the ring nitrogen atom or to the ring carboxy substituent. The halo substituent representing $R^1$ or $R^2$ may be chlorine, bromine, iodine or fluorine; chlorine or bromine being preferred.

The pharmaceutically acceptable cations representing M are those derived from bases which yield a pharmaceutically acceptable salt of the open ring compounds. The salts may be derived from either inorganic or organic bases to yield ammonium salts; alkali metal salts (sodium, potassium, etc.); alkaline earth salts, preferably calcium or magnesium; dicyclohexylamine salts, lower alkylamine salts; di(lower)alkylamine salts; tri (lower)alkylamine salts and the corresponding omega-hydroxy analogues (e.g. methylamine, ethylamine, propylamine, dimethylamine, diethylamine, dipropylamine, trimethylamine, triethylamine, tripropylamine, di(hydroxyethyl)amine, and the like). Similarly more complex amines which are employed in depot administration for slow release into the body, such as N,N[1]-dibenzylethylenediamine, are applicable bases for pharmaceutically acceptable salt formulation.

The compounds of this invention are produced by acylation of the aryl substituted 2-carboxy-heterocyclic amine precursor of the formula:

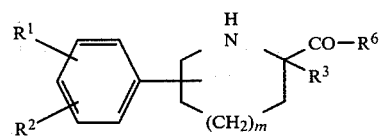

where $R^1$, $R^2$, $R^5$, $R^6$ and m are defined above, in aqueous alkaline solution with a substituted alkanoic acid halide of the formula:

$$XCO(CHR^4)_nCH_2Y$$

where X is chloride or bromide;
  $R^4$ and n are defined above and
  Y is chloro, bromo, alkanoylthio of 2 to 6 carbon atoms or aroylthio of 6 to 10 carbon atoms.

Where Y is chloro or bromo, the intermediate product is reacted with an alkali metal salt of a thioalkanoic acid or thioaromatic acid to introduce the mercapto function in the terminal position represented by Y.

Ring closure between the 2-carboxyl group and the mercapto substituent representing Y is accomplished by conventional activation of the carboxyl group, e.g. as an activated ester, mixed anhydride, carbodiimide, acyl halide, etc. The use of N, N[1]-dicyclohexylcarbodiimide (DCC) is a preferred activating reagent because of the facility of the ring closure and ease of removal of the dicyclohexyl urea by product.

The compounds of this invention contain two chiral centers in the nitrogen containing heterocyclic ring, specifically the carbon atom to which the carboxy substituent is attached (α-carbon of proline) and the carbon atom to which the phenyl substituent is attached (either the β or δ-carbon of proline). Hence, by selection or preparation of a proline or homoproline reactant of known relative stereoconfiguration, the final product obtained is limited to a dl-mixture of stereoisomers-(epimers) which are separable by standard methods of resolution when the reactant $XCO(CHR^4)_nCH_2Y$ contains no additional chiral center (i.e., $R^4$ is hydrogen). Where the alkanoic acid halide $NCO(CHR^4)_nCH_2Y$ contains a chiral center, i.e. $R^4$ is other than hydrogen, diastereoisomers are formed which are readily separated by conventional methods such as fractional crystallization, chromatography or fractional distillation.

The pharmaceutically acceptable salts of the 3-carboxy isoquinoline compounds are produced in a conventional manner by neutralization of the acid with an equivalent of the desired base.

The starting compounds for production of the compounds disclosed herein are either known or readily preparable by the chemist employing known techniques.

The compounds of this invention inhibit the conversion of angiotensin I to angiotensin II, thereby alleviating hypertension caused by the strong pressor action of the latter octapeptide. The compounds are administered to the hypertensive animal in single or divided doses, orally or parenterally, at a dose from about 0.1 to 150 milligrams per kilogram per day. The preferable dosing regimen provides from about 1 to 50 milligrams per kilogram per day, depending upon the severity of the hypertensive state. Oral administration in solid form by tablet or capsule may be accomplished with the compounds of this invention in neat or pure form alone or in combination with conventional adjuvants. Similarly, parenteral administration may be accomplished with physiological saline or via suspension in conventional vehicles. In any event, the dosing regimen must be individualized by the attending physician for the patient based upon the severity of the dysfunction.

The activity of the compounds of this invention was established by incubation of hippuryl-L-histidyl-L-leucine at 37° C. with angiotensin converting enzyme by the following procedure:

A crude angiotensin converting enzyme supernatant is obtained by blending 1 gm. of rabbit lung acetone powder (PelFreez Biologicals) with 35 ml of 50 mM (buffered) potassium phosphate, pH 8.3 and centrifuging for 45 min. at 40,000 xg.

The specific angiotensin converting enzyme substrate Hippuryl-L-histidyl-L-leucine (HHL-Sigma Chem. Co.) is prepared at 5 mM in 200 mM potassium phosphate buffer containing 757 mM NaCl at pH 8.3.

Incubation for the assay of HHL hydrolysis by angiotensin converting enzyme is carried out in a 37° C. gyrorotary incubator in disposable 13×100 mm tubes. Each 0.25 ml assay mixture contains the following components at the final concentrations: potassium phosphate buffer, 100 mM; NaCl, 300 mM; HHL, 5 mM; and enzyme 0.15 ml (10 mU approx.) added last to initiate the reaction. Zero time controls have 0.25 ml of 2N HCl added before the enzyme. The timed reactions are terminated with acid at 30 min. similarly and the hippuric acid freed from substrate is extracted into 1.5 ml of ethylacetate by vortex mixing for 15 sec. After 5 min. centrifugation in a clinical centrifuge, a 1.0 ml aliquot of the ethyl acetate layer is transferred to a clean tube. These aliquots are evaporated to dryness by heating (120° C.) in a Temp-Block module heater.

The hippuric acid is resuspended in 1.0 ml of water, the absorbance at 228 nm is determined, and the amount present is calculated from a standard curve. The amount of hippuric acid ×1.1 (extraction coefficient) ×1.5 (ratio of volumes) ×1 µM hippuric acid/200 µg ×1/30 min.=nM hippuric acid released/min. Enzyme activity in the presence of an inhibitor is compared with control activity, and reported as a percentage inhibition. (Cushman, D. W. and Cheung, H. S., Biochem. Pharmacol. 20 1637 (1971).

The in vitro experiments were confirmed following the procedure of Rubin et al, J. Pharmacol. Exp. Ther 204 721 (1978) whereby jugular vein and carotid artery cannulae are placed in an ether anesthetized, normotensive, male, Spraque-Dawley rat for injection of compounds and direct recording of systemic arterial pressure, respectively. The blood pressure responses in the conscious animal to i.v. injections of angiotensin I (300 ng/kg), angiotensin II (100 ng/kg) and bradykinin (10 µg/kg) are recorded and compared with identical doses administered at various time intervals after oral dosing of the angiotensin converting enzyme inhibitor of this invention.

In addition, the blood pressure lowering ability of the compounds of this invention was established by measuring the systolic pressure of male spontaneously hypertensive rats with a Decker Caudal Plethysmograph. The compounds tested were administered orally and blood pressure was read prior to and at 1.5, 4 and 24 hours after drug administration.

As representative compounds of the invention, 100 nanograms per milliliter of the product of Example two, infra, inhibited angiotensin converting enzyme by 40 percent (three determinations) in the above described in vitro test and demonstrated marked inhibition in vivo (72%) at 10 milligrams per kilogram dose, 10 minutes post dosing (mean two animals) and reduced the blood pressure of the standard experimental rat by 23 mmHg at 50 mg/kg orally administered. Similarly, 100 nanograms per milliliter of the product of Example four inhibited angiotensin converting enzyme by 72 percent (12 determinations) in vitro, and demonstrated marked inhibition in vivo (65%) at 10 mg/kg, oral, 10 minutes post dosing (mean two animals) and reduced the blood pressure of the standard experimental rat by 21 millimeters at four hours after administration of a 50 milligram per kilogram oral dose.

The α-acid of Example 7 demonstrated borderline inhibition of angiotensin converting enzyme of 5 percent at 100 ng/ml and 17 percent at 1000 ng/ml, in vitro. The β-acid of Example 7, on the other hand, demonstrated marked activity in vitro at concentrations of 1 mg/ml (20 percent inhibition); 10 ng/ml (40 percent inhibition); 50 ng/ml (75 percent inhibition); 100 ng/ml (84 percent inhibition); and 1000 ng/ml (99 percent inhibition) and reduced blood pressure in the rat by 37 mmHg at 10 mg/kg, oral. Thus, surprisingly, substantially all of the activity in the product of Example 7 is found in the β-acid epimer.

The following examples illustrate the preparation of representative compounds of this invention.

EXAMPLE 1 cis-1-(5-Acetylthiopropanoyl)-5-(5,4-dimethoxyphenyl)proline

To a solution of cis-5-(3,4-dimethoxyphenyl)proline hydrochloride (8.0 g., 0.028 m) and sodium hydroxide (2.22 g., 0.055 m ) in water (50 ml.) at 10° C., was slowly added 3-bromopropionyl chloride (2.80 ml., 0.028 m) along with sodium hydroxide (1.11 g., 0.028 m) in water (25 ml.), keeping pH between 7.5 and 9. This mixture was stirred at 25° C. overnight. Potassium thioacetate, prepared by mixing thiolacetic acid (1.50., 0.021 m) and potassium carbonate (1.75 g., 0.012 m) in water (15 ml.) was added to the reaction which was stirred overnight at 25° C. to afford the title compound, which was employed without isolation as the reactant in the following example.

EXAMPLE 2 cis-1-(3-Mercaptopropanoyl)-5-(3,4-Dimethoxyphenyl)proline

Ammonium hydroxide (5 ml.) was added to the reaction product of Example 1 and stirred at 25° C. for 2 hours. A precipitate was obtained upon acidification with dillute hydrochloric acid. After the solid was filtered off it was dissolved in methylene chloride, washed with brine, dried over sodium sulfate and the solvent evaporated off to give the title compound as a white solid, m.p. 69°–75° C.

Analysis for: $C_{16}H_{21}NSO_5.0.5\ CH_2Cl_2$
Calculated: C, 51.83; H, 5.80; N, 3.66;
Found: C, 52.07; H, 5.68; N, 5.78.

EXAMPLE 3 cis-1-(3-Benzoylthiopropanoyl)-5-phenyl proline

To a solution of cis-5-phenyl proline hydrochloride (5.0 g., 0.022 m) and 1 N sodium hydroxide (44 ml.) at 10° C. was slowly added 3-bromopropionyl chloride (2.2 ml., 0.022 m) and 2-N sodium hydroxide (11 ml.), keeping pH between 7.5 and 9. The mixture was stirred at 25° C. for 3 hours. Potassium thiobenzoate, prepared by mixing thiobenzoic acid, 95% (3.28 g., 0.024 m) and potassium carbonate (2.02 g., 0.014 m) in water (25 ml.), was added to the reaction, which was stirred overnight at 25° C. The solution was acidified and extracted with ethylacetate. The extract was washed, dried over sodium sulfate and the solvent was evaporated off to yield the title compound as a gum which was employed as the reactant in the following example without further purification.

EXAMPLE 4 cis-1-(3-Mercaptopropanoyl)-5-phenyl proline

This product from Example 3 was added to a solution of methanol saturated with ammonia and was stirred at 25° C. for 2 hours. The solvent was evaporated off, leaving a solid which was stirred in water and filtered. The filtrate was extracted five times with diethyl ether and was acidified. The acidified solution was then extracted with methylene chloride, washed with brine, dried over magnesium sulfate and concentrated to a solid. This residue was extracted with hot hexane from which the title compound crystallized, m.p. 61°–64° C.

Analysis for: $C_{14}H_{17}NSO_3$
Calculated: C, 60.19; H, 6.14; N, 5.02;
Found: C, 60.34; H, 5.99; N, 5.04.

EXAMPLE 5 trans-Hexahydro-7(3,4-dimethoxyphenyl)-1H,5H-pyrrolo[2,1-c][1,4]thiazepine-1,5-dione The compound produced in Example 2 is dissolved in about 500 milliliters methylene chloride and the solution is chilled under nitrogen to 15° C. in a dry ice-acetone mixture. 4-Dimethylaminopyridine is added and the mixture is stirred for five minutes. A slight excess of dicyclohexylcarbodiimide dissolved in methylene chloride is added with stirring. The chilled source is removed after 15 minutes and the solution is stirred overnight at room temperature. The volume of the reaction mixture is reduced on a rotary evaporator under reduced pressure to about 100 milliliters. A precipitate is removed by filtration and the filter residue is washed several times with methylene chloride. The filtrate and combined washings are washed successively with 1N HCl, saturated aqueous $NaHCO_3$, water and saline and the solution is dried over $MgSO_4$. Evaporation of the methylene chloride with a rotary evaporator under reduced pressure yields the title compound.

EXAMPLE 6 trans-Hexahydro-7-phenyl-1H,5H-pyrrolo[2,1-c][1,4]thiazepine-1,5-dione

Following the procedure of Example 5 with the exception that the reactant to be cyclized is the product of Example 4, affords the title compound.

EXAMPLE 7

α-and β-5-Phenyl-1-(3-benzoylthio-2-methyl-1-oxopropyl)-proline

To a solution of cis-5-phenyl proline hydrochloride (30.0 g., 0.13 m) and sodium hydroxide (10.4 g., 0.26 m) in water (600 ml.) at 10° C. was slowly added (-) 3-benzoylthio-2-methyl propionyl chloride (51.42 g., 0.13 m). At the same time, from a separate dropping funnel, was added a solution of sodium hydroxide (5.2 g., 0.13 m) in water (70 ml.) at such a rate that the solution was maintained at a pH between 9.5 and 7.5 pH units (final pH 7.5). After stirring overnight at 5° C., the reaction mixture was filtered and the clear filtrate acidified with dilute hydrochloric acid. The product was extracted into diethyl ether. A solid (2.65 g) precipitated from the ether extract. This material was recrystallized from acetonitrile giving the α-acid as a white solid, m.p. 194°–195° C., $[\alpha]_D^{24.5}=0$, (C=93%,MeOH)

Analysis for: $C_{22}H_{23}NSO_4$
Calculated: C, 66.47; H, 5.83; N, 3.52;
Found: C, 66.30; H, 5.86; N, 3.60.

The diethyl ether filtrate was washed with brine, dried over anhydrous sodium sulfate and filtered. A white solid crystallized from the ether solution, 5.60 g. The product was recrystallized from acetontrile to give the β-acid m.p. 148°–149° C., $[\alpha]_D^{24.5}=0$ (C=0.78%, MeOH)

Analysis for: $C_{22}H_{23}NSO_4$
Calculated: C, 66.47; H, 5.83; N, 3.52
Found: C, 65.96; H, 5.79; N, 3.79

EXAMPLE 8

α-and β-5-phenyl-1-(3-mercaptopropanoyl) proline

Each of the compounds of Example 7 is treated with ammonium hydroxide and worked up in accordance with the procedure of Example 2 to afford the title compound.

What is claimed is:

1. A compound of the formula:

$$R^1, R^2\text{-phenyl}-N(-CH_2-(CH_2)_m-CR^3(-C(=O)-S))-C(=O)-(CHR^4)_n-CH_2$$

wherein
R[1] and R[2] are independently, hydrogen, alkyl of one to six carbon atoms, alkoxy of one to six carbon atoms or halo;

$R^3$ is hydrogen or alkyl of one to six carbon atoms;

$R^4$ is hydrogen or alkyl of one to six carbon atoms;

m is one of the integers 0 or 1; and n is one of the integers 0, 1 or 2.

2. A compound of claim 1 of the formula:

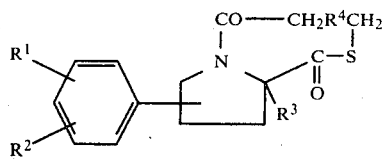

wherein
$R^1$ and $R^2$ are, independently, hydrogen or alkoxy of one to three carbon atoms;
$R^3$ is hydrogen or methyl; and
$R^4$ is hydrogen or alkykl of one to three carbon atoms.

3. A compound of claim 1 which is trans-hexahydro-7(5,4-dimethoxyphenyl)-1H,5H-pyrrolo[2,1-c][1,4]thiazepine-1,5-dione.

4. A compound of claim 1 which is trans-hexahydro-7-phenyl-1H,5H-pyrrolo[2,1-c][1,4]thiazepine-1,5-dione.

* * * * *